United States Patent
Brugger et al.

(10) Patent No.: US 6,572,641 B2
(45) Date of Patent: Jun. 3, 2003

(54) DEVICES FOR WARMING FLUID AND METHODS OF USE

(75) Inventors: James M. Brugger, Newburyport, MA (US); Jeffrey H. Burbank, Boxford, MA (US); Dennis M. Treu, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 09/829,670

(22) Filed: Apr. 9, 2001

(65) Prior Publication Data

US 2002/0147481 A1 Oct. 10, 2002

(51) Int. Cl.$^7$ .................................................. A61F 7/00
(52) U.S. Cl. ........................................ 607/106; 607/113
(58) Field of Search .......................... 607/104, 105, 607/106, 113

(56) References Cited

U.S. PATENT DOCUMENTS 4,976,685 A * 12/1990 Block, Jr. ................... 604/122
5,420,962 A * 5/1995 Bakke ......................... 392/379
6,175,688 B1 * 1/2001 Cassidy et al. ............. 392/470
2001/0010802 A1 * 8/2001 Tamari ......................... 422/41
2001/0011585 A1 * 8/2001 Cassidy et al. ............... 165/46

* cited by examiner

Primary Examiner—Harold Joyce
(74) Attorney, Agent, or Firm—Proskauer Rose LLP

(57) ABSTRACT

An external fluid warming device is described that includes a fluid warming chamber and an air separation chamber. The fluid warming chamber has a fluid inlet that communicates with a fluid pathway. The air separation chamber that communicates with the fluid pathway has a fluid outlet and a gas outlet. A heating source, such as heat plates, are disposed adjacent the fluid pathway for transferring heat to the fluid. In use, the air separation chamber is positioned above the fluid warming chamber and the heating source. The fluid inlet is connected to a source of fluid and the fluid outlet is connected to an output device, such as an ultrafiltration machine. Gas generated during warming of the fluid collects at a top of the air separation chamber and is vented through the gas outlet, whereas fluid passes through a bottom of the air separation chamber and through the fluid outlet.

19 Claims, 4 Drawing Sheets

DEVICES FOR WARMING FLUID AND METHODS OF USE

FIELD OF THE INVENTION

The present invention relates generally to medical devices useful for externally warming fluid or blood products prior to infusion into a patient's body cavity or vessel. More particularly, the devices minimize air embolization by removing gaseous material generated during the warming process.

BACKGROUND OF THE INVENTION

Patients undergoing blood or fluid processing, e.g., hemofiltration, hemodialysis, hemodiafiltration, ultrafiltration, peritoneal dialysis, or infusion of saline, drugs, or nutritional fluid, are at risk for hypothermia in the absence of warming the fluids infused into the patient's blood stream or peritoneum. Hypothermia, defined as body temperature significantly below normal, typically at 98.6° F. (37° C.), is of considerable importance because it can represent a medical emergency requiring aggressive treatment. Causes of hypothermia are usually classified into three categories: (1) accidental hypothermia, (2) hypothermia due to acute illness, and (3) immersion hypothermia.

Accidental hypothermia usually occurs in elderly or inebriated individuals after prolonged exposure to low external temperature, e.g., during winter months. Patients with body temperature below 85 and 90° F., usually appear pale and cold with stiff musculature. Patients having body temperature below 80° F. are usually unconscious with shallow and slow respiration, bradycardia, and hypotension. Patients having body temperature below 77° F. are usually comatose and areflexic. Hemoconcentration, azotemia, metabolic acidosis, and cardiac arrythmias can occur in these patients. Moderate hypothermia in association with acute illnesses including congestive heart failure, uremia, diabetes mellitus, drug overdose, acute respiratory failure, and hypoglycemia, is usually found in elderly and hospitalized patients. These patients usually have metabolic acidosis and cardiac arrythmia. Most of them are comatose. In immersion hypothermia, there is great variability in each individual's ability to tolerate heat loss in cold water. A lean person generally is less able to tolerate a fall in temperature than an obese swimmer. In hypersensitive individuals, immersion in cold water may cause vascular spasm, vomiting, and syncope.

In addition to maintaining adequate airway and cardiovascular support in hypothermia patients, the main treatment for each type of hypothermia constitutes rewarming the body. In treating patients with mild hypothermia, external rewarming using a warm blanket or placing the patient in a warm room is usually sufficient. However, patients with moderate to severe hypothermia require reestablishment of body core temperature. This is usually achieved by placing the patient in a warm bath or a Hubbard tank at 104 to 108° F. Unfortunately, external warming tends to dilate constricted peripheral blood vessels, thereby shunting blood away from the internal organs. In patients with severe hypothermia, external warming may lead to rewarming shock and may not be sufficient to warm the myocardium to allow antiarrythmic agents to take effect. In this situation, hemodialysis, peritoneal dialysis, or ultrafiltration, where blood or dialysate is warmed externally, can be used. Warmed intravenous fluid, such as glucose and saline, low molecular-weight dextran, or albumin, can be used to maintain blood volume and facilitate warming of core temperature. Unfortunately, current external devices for warming intravenous fluid suffer a significant drawback in that air or gaseous material that arises as a result of warming can reach the patient's blood stream and cause air embolization, resulting in organ ischemia or infarction.

Therefore, devices and methods useful for treating and/or preventing hypothermia, or to maintain patient comfort, are needed that allow warming of fluid which can be infused intravenously or be used in conjunction with hemodialysis, peritoneal dialysis, or ultrafiltration, during which risk of air embolization is eliminated or minimized.

SUMMARY OF THE INVENTION

The present invention provides devices and methods for pre-infusion external warming of fluids, such as saline, lactated Ringer's solution, dialysate, or blood, for infusion therapy, including hemofiltration, hemodialysis, ultrafiltration, hemodiafiltration, or peritoneal dialysis. It will be understood that the devices and methods disclosed herein can also be used in treating patients with hypothermia or in critically ill patients to prevent hypothermia. The devices remove air or gaseous material generated during the warming process, thereby minimizing risk of air embolization that causes organ ischemia or infarction, e.g., in the lungs.

In a first embodiment, the device includes an air separation chamber that is oriented above a fluid warming chamber. The fluid warming chamber has an inlet that communicates with a fluid pathway adapted for transfer of heat from a heating mechanism to the fluid. In certain embodiments, the fluid inlet is at a bottom of the fluid warming chamber. The air separation chamber, in communication with the fluid pathway, includes a fluid outlet and a gas outlet. The air separation chamber typically lies above the heating mechanism so that air or gaseous material generated during the warming process rises to the top of the air separation chamber. In certain embodiments, the air separation chamber also includes a partition that separates the fluid outlet from the gas outlet to minimize escape of gas into the infusion line. In other embodiments it does not.

In another embodiment, the device includes a heating mechanism comprising first and second heat plates. The first heat plate is disposed adjacent to the fluid pathway. The second heat plate is disposed adjacent to the fluid pathway and opposite the first heat plate so that the fluid pathway is sandwiched between the first and second heat plates. Fluid in the pathway is warmed by heat generated from the heat plates. In other embodiments a support wall is disposed adjacent to the fluid pathway and opposite the first heat plate so that the fluid pathway is sandwiched between the first heat plate and the support wall.

In other embodiments, the fluid flows through the fluid pathway of the fluid warming chamber at a substantially higher rate than the fluid flows through the air separation chamber. This difference in flow rate can be accomplished simply by providing a fluid pathway with a smaller diameter channel than the channel of the air separation chamber. The fluid will therefore slow substantially upon exiting the fluid pathway of the fluid warming chamber and entering the air separation chamber. A diminished rate of flow through the air separation chamber facilitates de-gassing of the fluid, and ensures that small bubbles are not swept into the fluid outlet.

It will be understood that the devices and methods of the invention provide a safety mechanism to guard against overheating when fluid flow stops momentarily. When fluid in the fluid pathway stops, it will heat above the set point. The air separation chamber, however, is typically independent of the heating source, and therefore extra fluid in the air separation chamber remains at a lower temperature. When flow resumes, hot fluid from the fluid pathway mixes with low temperature fluid in the air separation chamber. The low temperature fluid in the air separation chamber thereby buffers the temperature of fluid exiting the warming system. This feature serves to reduce the extent of overheating.

In use, a fluid source is connected to the fluid inlet of the warming bag, and an output device, such as a hemofiltration, hemodialysis, hemodiafiltration, ultrafiltration, or peritoneal dialysis machine, is connected to the fluid outlet. Fluid flows from the source through the fluid inlet and through the fluid pathway of the fluid warming chamber. One or more heat plates surrounding the fluid pathway heat the fluid as it flows through the fluid pathway. The temperature of the heat plates or other heat source and the flow rate are adjusted by an operator comfort setting to obtain an appropriate temperature. Fluid passes through the fluid pathway into the air separation chamber where, in certain embodiments, the flow rate slows. Gas bubbles rise in the air separation chamber and collect at the top of the air separation chamber. Gas is periodically vented through a gas outlet. The fluid, while de-gassing, flows through the lower part of the air separation chamber and through the fluid outlet to an output device.

It will further be understood that there are several advantages to using the fluid warming devices and methods described herein. For example, the devices and methods (1) improve patient comfort during infusion therapies by providing external warming of fluid and blood products prior to their administration to a patient, (2) protect against hypothermia in patients receiving a large volume of intravenous fluid, e.g., patients undergoing hemofiltration, hemodialysis, hemodiafiltration, or ultrafiltration, (3) provide a treatment alternative for patients with hypothermia, and (4) avoids the need for a separate drip chamber.

DETAILED DESCRIPTION

Figure 1A:
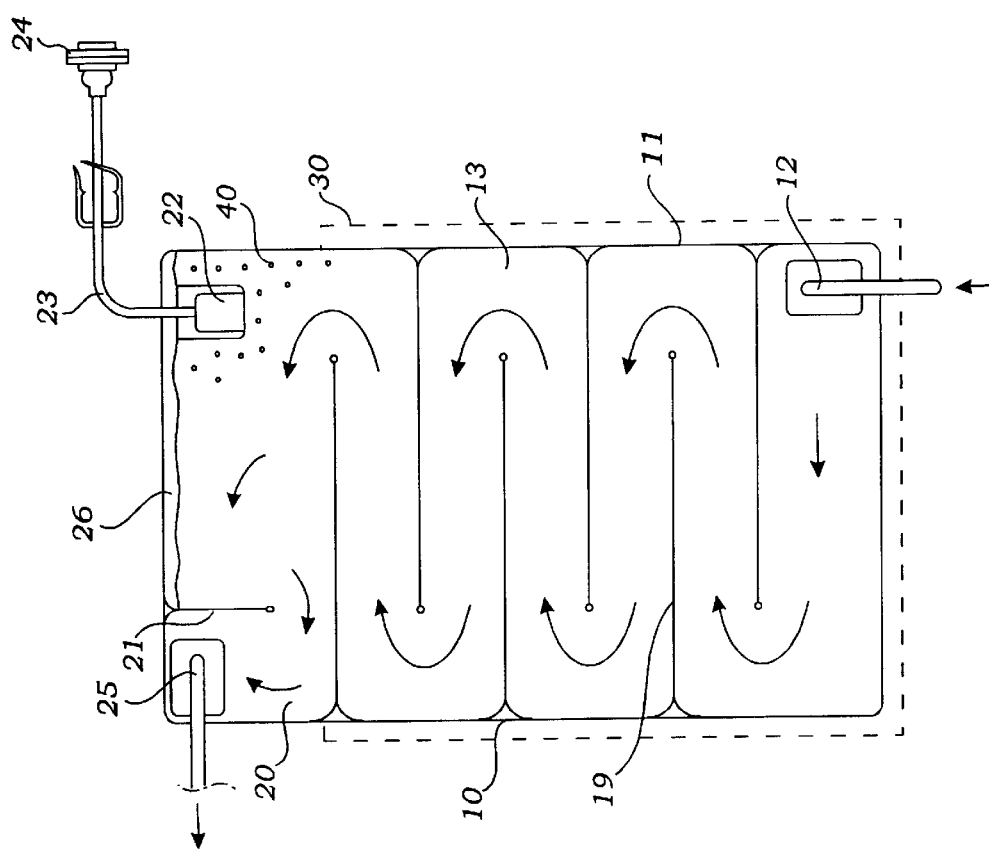
FIG. 1A depicts a fluid warming device in accordance with the present invention.

A fluid warming device as disclosed herein is depicted in FIG. 1A. Here, the device takes the form of a fluid warming bag or panel 10 comprised of first and second layers of material, e.g., flexible plastic bonded together, e.g., by RF or heat welding. Panel 10 includes fluid warming chamber 11 and air separation chamber 20. Fluid warming chamber 11 comprises fluid inlet 12 that communicates with fluid pathway 13. Fluid pathway 13 is formed from flow path partitions 19, and is adapted for heat transfer from an adjacent heating element, e.g., one or more heat plates 30. Air separation chamber 20 communicates with fluid pathway 13. Air separation chamber 20 has fluid outlet 25 and gas outlet 22 that communicates with tubing 23 and terminates in transducer protector 24 which allows the passage of gas but not liquid. Air separation chamber 20 includes, in the depicted embodiment, partition 21 that prevents gas that collects in area 26 of air separation chamber 20 from reaching fluid outlet 25.

In use, the fluid warming bag depicted in FIG. 1A is oriented with air separation chamber 20 on top and fluid warming chamber 11 on bottom. Fluid enters warming bag 10 through inlet 12 and passes through fluid pathway 13. The fluid passing through fluid pathway 13 is warmed by one or more heat plates 30 (see FIG. 1B) disposed adjacent panel 10. Flow rate and temperature of heat plates 30 are adjusted so that fluid achieves the desired temperature while passing through fluid pathway 13. Warm fluid having gas bubbles 40 enters air separation chamber 20. Gas bubbles 40 collect at top 26 of air separation chamber 20. Warm fluid passes through the bottom of the air separation chamber 20, and exits the fluid warming bag through fluid outlet 25. Accumulated gas collects at top 26 and is periodically released through gas outlet 22, tube 23, and transducer protector 24. Transducer protector 24 permits passage of air, but acts as a valve that closes when contacted by fluid. Positive fluid pressure against the transducer protector ensures that air is not sucked into the system through the transducer protector.

Figure 1B:
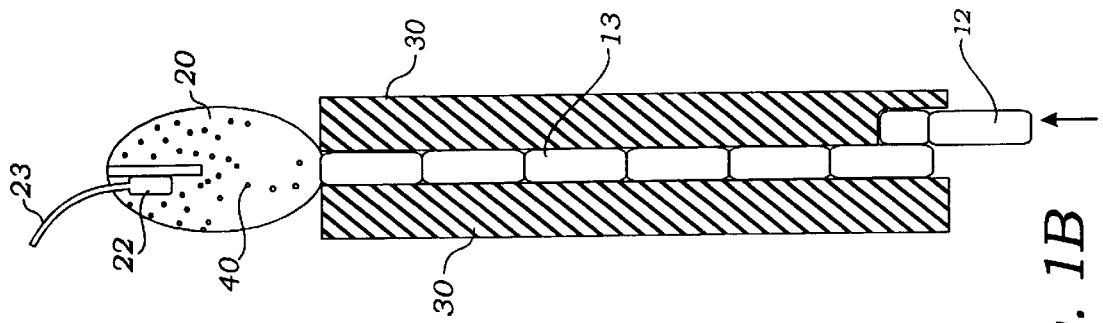
FIG. 1B depicts a lateral view of the fluid warming device of FIG. 1A.

FIG. 1B shows a lateral view of the fluid warming device depicted in FIG. 1A. Here, first and second heat plates 30 are arranged with a gap between the heat plates. Fluid pathway 13 of panel 10 lies within the gap so that heat plates 30 warm the fluid delivered through fluid pathway 13. Air separation chamber 20 is, in certain embodiments, situated above fluid pathway 13, and lies outside the gap and above heat plates 30 so that air separation chamber 20 is not heated. Flow rate through a passage is a function of lumenal diameter of the passage. Air separation chamber 20 has, in the depicted embodiment, a much larger diameter than fluid pathway 13. Therefore, fluid flows more rapidly through the fluid pathway 13 and slows substantially when the fluid reaches the larger-diameter air separation chamber 20. Diminished flow rate in air separation chamber 20 allows bubbles 40 to rise and accumulate at area 26 of air separation chamber 20, and ensures that the bubbles are not swept into fluid outlet 25.

Figure 1C:
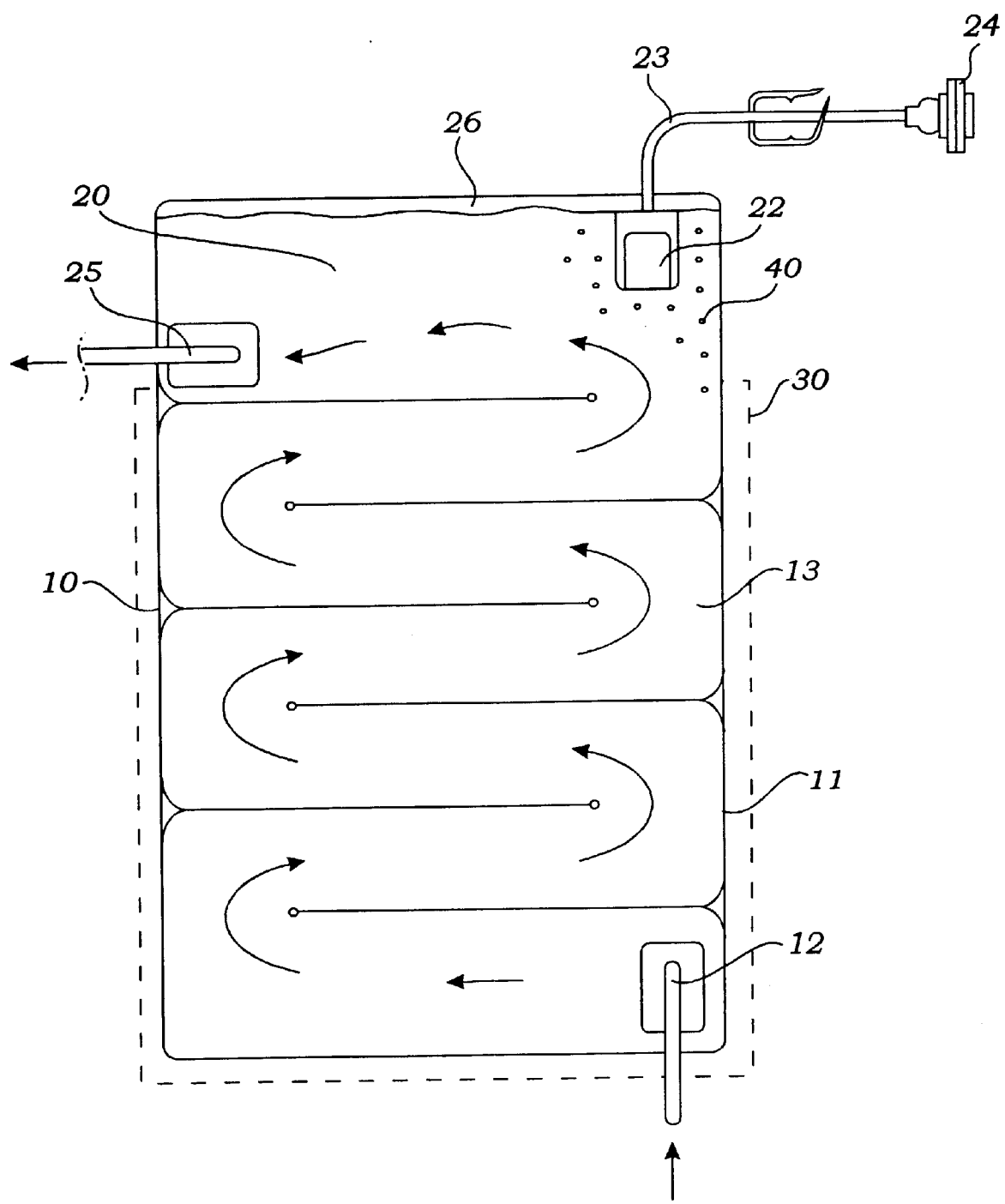
FIG. 1C depicts another embodiment of a fluid warming device and air separation chamber.

FIG. 1C depicts another embodiment of the fluid warming device without partition 21 in the air separation chamber 20. Fluid outlet 25 is included in the bottom of air separation chamber 20. This design is particularly useful to facilitate removal of air bubbles detected in the replacement fluid outlet line. When an air bubble is detected in the outlet line, the fluid is reversed back into the warming device to eliminate the bubble. However, in the device depicted in FIG. 1A having partition 21 and fluid outlet 25 located in the top of the separation chamber, on reversal air is trapped in the outlet bond socket. When replacement fluid runs forward again, the bubble again passes down the fluid outlet line. By having fluid outlet 25 at the bottom of the air separation chamber and by eliminating partition 21, air detected in the fluid line can be returned to air separation chamber 20 and trapped at the top of the chamber.

Figure 2:
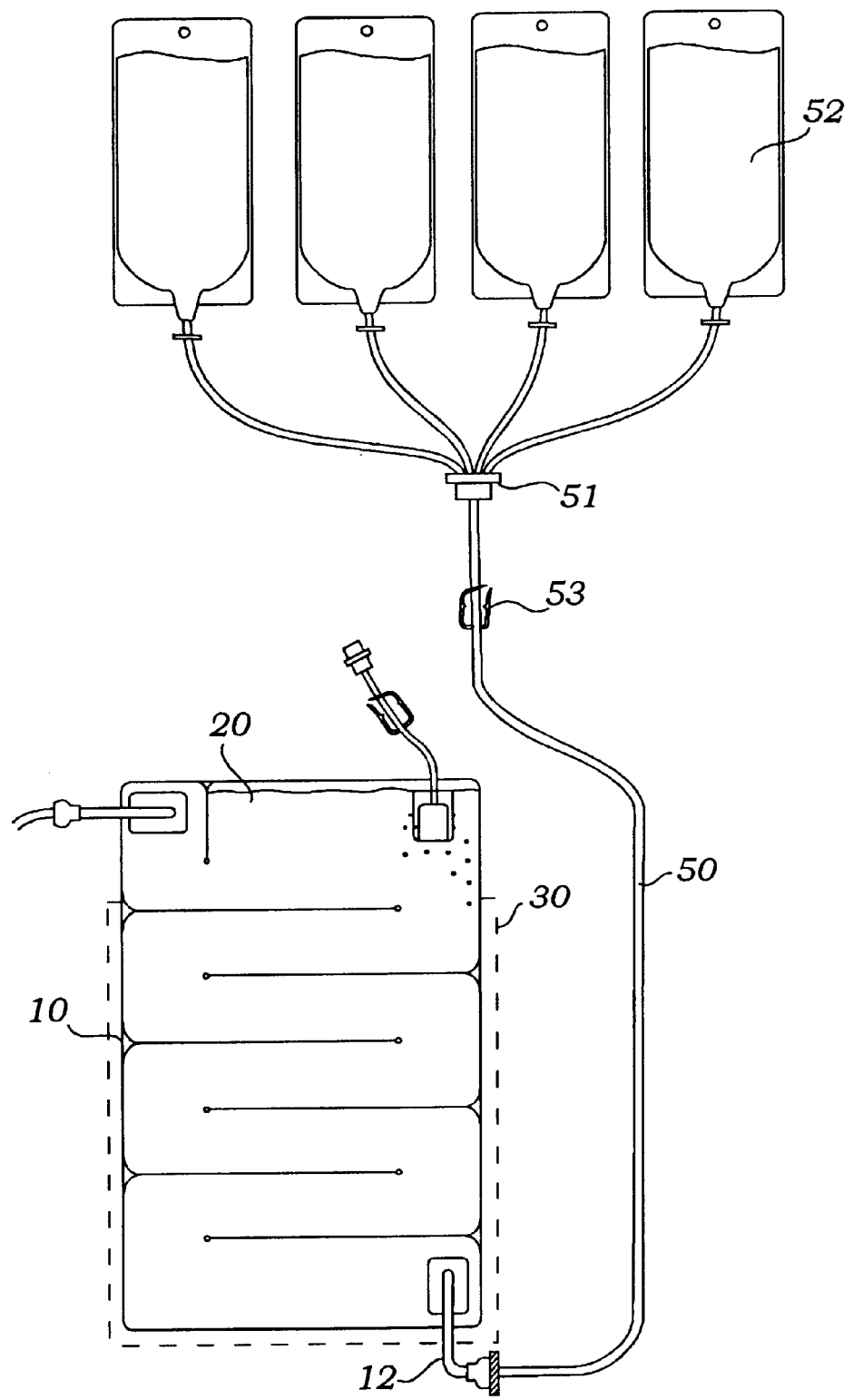
FIG. 2 depicts the fluid warming device of FIG. 1A connected to a source of fluid.

FIG. 2 depicts warming device 10 connected to fluid input 50. Input line 50 receives fluid, e.g., saline or Ringer's lactate from intravenous bags 52, which are joined at fluid regulator 51. Input line 50 is provided with clamp 53 for stopping flow of fluid before, during, or after connection to fluid inlet 12.

Figure 3:
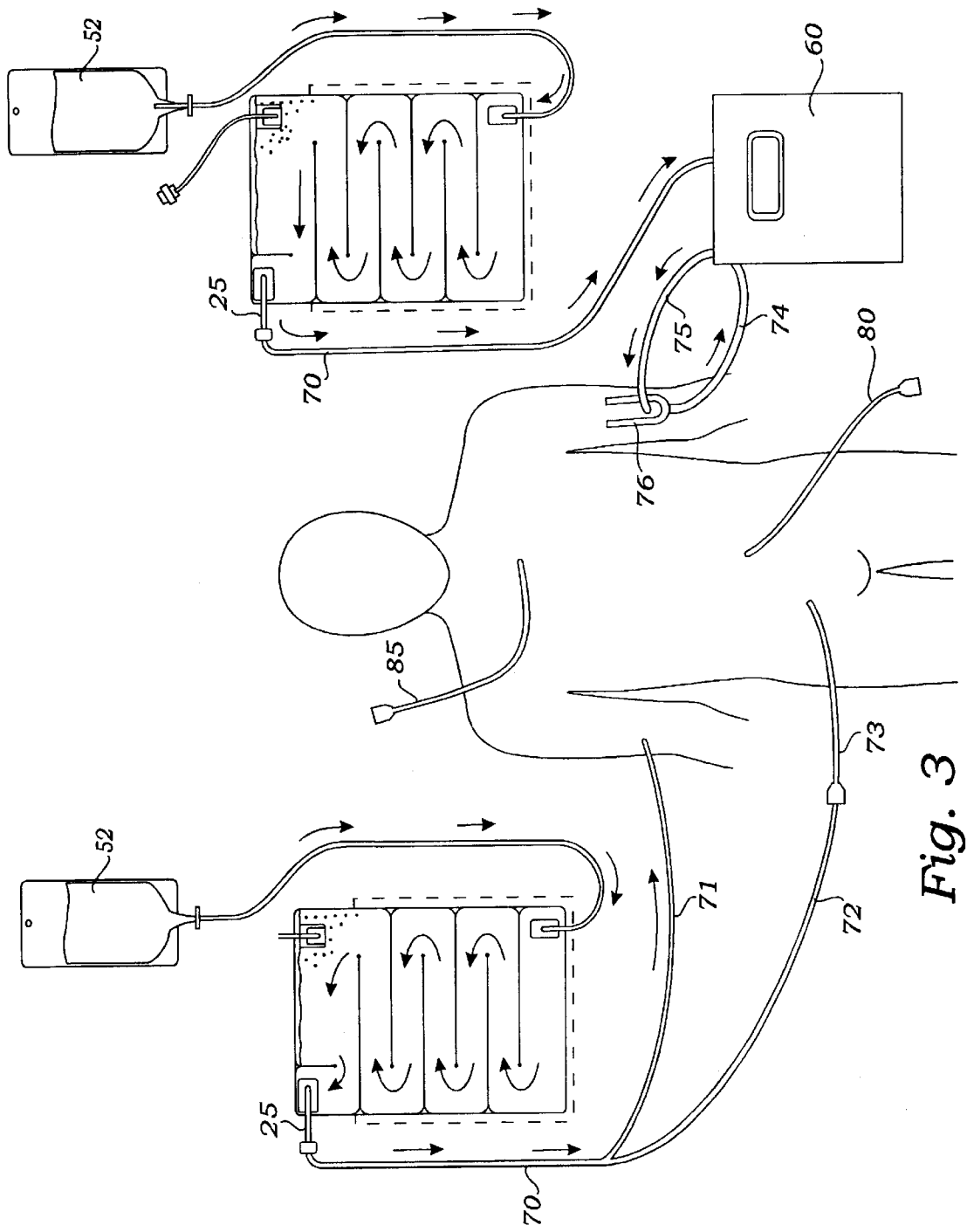
FIG. 3 depicts the use of the fluid warming device of FIG. 1A for administration of fluid to a patient.

FIG. 3 depicts the use of the fluid warming device in a variety of therapeutic applications. For example, fluid output line 70 connects proximally to fluid outlet 25, and inserts distally through distal tubing 71 into a patient's right brachial vein. Alternatively, fluid output line 70 connects proximally to fluid outlet 25, and inserts distally through distal tubing 72 into a central venous catheter, such as femoral catheter 73 or right subclavian venous catheter 85. In another alternative, output line 70 connects distally with device 60, e.g., a device for hemofiltration, hemodialysis, hemodiafiltration, or ultrafiltration. Device 60 is connected to the patient's arteriovenous shunt 76. Blood is received from the arteriovenous shunt through tubing 74, and is returned to the arteriovenous shunt through tubing 75. In still another alternative, device 60 for use in peritoneal dialysis is connected to peritoneal catheter 80 that is inserted in the patient's peritoneal cavity. Replacement fluid, for example, is provided by intravenous bag 52 and is warmed before mixing with blood or peritoneal fluid for delivery to the patient through tubing 75.

With reference to FIG. 1A, panel 10 may be dimensioned from approximately 8 to 11 inches in height and approximately 5 to 6 inches in width. The panel may be constructed of RF welded sheets of polyvinylchloride (PVC), each sheet having a thickness of approximately 0.011 inches. The channels that form fluid pathway 13 are produced by RF welding of the sheets. Air release through gas outlet 22 occurs when approximately 5 cc of air collects at area 26 of air separation chamber 20. With reference to FIG. 1B, the gap between heat plates 30 may be approximately 0.06 inches to approximately 0.120 inches, preferably approximately 0.090 inches. The fluid volume of the heated areas is calculated as 0.01 cm thick×15 cm tall×13 cm wide, equaling approximately 19.5 cc. The estimated volume of air separation chamber is calculated as 75 cc minus 5 cc of air, equaling approximately 70 cc. Referring to FIG. 2, intravenous bags 52 may be suspended approximately 18 inches above the top of air separation chamber 20, giving an 18 inch head height when the intravenous bags are empty. It will be understood that the higher the head height, the greater the pressure, the greater the contact force of the PVC panels to the heating plates, and the greater the heat transfer efficiency. The hydrostatic pressure from the hanging fluid bags forces the flexible walls of fluid warmer bag 10, i.e., the walls of fluid pathway 13, into intimate contact with the walls of the heater unit, i.e., heat plates 30. This contact ensures optimal heat transfer. Moreover, as noted above, the gap width between heat plates 30 is critical. If the width is too narrow, the flow rate requirement of approximate 250 mL/min cannot be met with a head height of 18 inches. If the gap is too wide, then flow through the tortuous fluid pathway 13 begins to channel, reducing heat transfer. The foregoing ranges are set forth solely for the purpose of illustrating typical device dimensions and operating parameters. The actual dimensions and parameters of a device constructed according to the principles of the present invention may obviously vary outside of the listed ranges without departing from those basic principles.

With regard to temperature buffering described earlier, if outlet temperature at 200 mL/min flow is 38° C., and the heat plate temperature is 45° C., then when flow stops, the fluid in air separation chamber 20 is 38° C. and the fluid in fluid pathway 13 between heat plates 30 is 45° C. Flow can stop due to machine 60 malfunction (unrelated to fluid heat). The flow is stopped until the operator resolves the situation and resumes therapy. When flow is resumed, the 45° C. fluid mixes with 38° C. fluid to produce an average temperature of 40° C. Current equipment limits the temperature of heating plates to 41° C. to avoid redundant safety monitoring. The system described herein is passive, and allows a simplified heater, safety control scheme by mixing a potentially hot fluid (45° C.) with a cool fluid (38° C.). This system is safe and allows for a smaller heat transfer area to achieve the required temperature.

Although the foregoing invention has, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments.

What is claimed is:

1. A device for warming fluid, comprising:
    a fluid warming chamber comprising a fluid inlet that communicates with a fluid pathway adapted for heat transfer; and
    an air separation chamber that communicates with the fluid pathway, the air separation chamber having a fluid outlet and a gas outlet,
    wherein, during use, the device is oriented with the air separation chamber above the fluid warming chamber, gas collects at a top of the air separation chamber and is vented through the gas outlet, and fluid passes through a bottom of the air separation chamber and through the fluid outlet.

2. The device of claim 1, wherein the fluid inlet is at a bottom of the fluid warming chamber.

3. The device of claim 1, further comprising one or more heat plates disposed adjacent the fluid pathway.

4. The device of claim 1, further comprising first and second heat plates disposed adjacent the fluid pathway, and wherein the first heat plate is arranged parallel to the second heat plate with a gap between the first and second heat plates, and wherein the fluid pathway lies within the gap.

5. The device of claim 4, wherein the air separation chamber lies above the gap.

6. The device of claim 1, wherein the fluid pathway is arranged in a zigzag pattern from the fluid inlet to the air separation chamber above the fluid warming chamber.

7. The device of claim 1, wherein the air separation chamber has a partition that separates the fluid outlet from the gas outlet.

8. The device of claim 1, wherein the gas outlet of the air separation chamber includes a transducer protector.

9. A device for warming fluid, comprising:
    a fluid warming chamber comprising a fluid inlet that communicates with a fluid pathway adapted for heat transfer;
    an air separation chamber that communicates with the fluid pathway, the air separation chamber having a fluid outlet and a gas outlet; and
    a first heat plate adjacent the fluid warming chamber.

10. The device of claim 9, further comprising a second heat plate adjacent the fluid warming chamber and opposite the first heat plate.

11. The device of claim 9, further comprising a support wall adjacent the fluid warming chamber and opposite the first heat plate.

12. The device of claim 9, wherein the fluid inlet is at a bottom of the fluid warming chamber.

13. The device of claim 9, wherein the fluid warming chamber lies within a gap between the first and second heat plates.

14. The device of claim 13, wherein the air separation chamber lies above the gap.

15. The device of claim 9, wherein the fluid pathway is arranged in a zigzag pattern from the fluid inlet to the air separation chamber above the fluid warming chamber.

16. The device of claim 9, wherein the air separation chamber has a partition that separates the fluid outlet from the gas outlet.

17. The device of claim 9, wherein the gas outlet of the air separation chamber includes a transducer protector.

18. The device of claim 1, wherein the fluid warming chamber comprises first and second sheets of PVC material bonded by RF wilding.

19. The device of claim 1, wherein the fluid warming chamber comprises flexible thermoplastic material bonded by heat welding.

* * * * *